(12) United States Patent
Desriac et al.

(10) Patent No.: US 9,956,262 B2
(45) Date of Patent: May 1, 2018

(54) **USE OF A BACTERIUM ISOLATED FROM THE GENUS *PSEUDOALTEROMONAS*, CYCLOLIPOPEPTIDES AND USES THEREOF**

(71) Applicants: CENTRE NATIONAL DE LA RECHERCHE SCIENTIFIQUE (C.N.R.S), Paris (FR); UNIVERSITE DE RENNES 1, Rennes (FR); UNIVERSITE DE BRETAGNE OCCIDENTALE, Brest (FR)

(72) Inventors: Florie Desriac, Bannalec (FR); Yannick Fleury, Quimper (FR); Patrick Le Chevalier, Clohars-Fouesnant (FR); Delphine Destoumieux, Viols-le-Fort (FR); Matthieu Simon, Rennes (FR)

(73) Assignees: CENTRE NATIONAL DE LA RECHERCHE SCIENTIFIQUE (C.N.R.S.), Paris (FR); UNIVERSITE DE RENNES 1, Paris (FR); UNIVERSITE DE BRETAGNE OCCIDENTALE, Brest (FR)

( * ) Notice: Subject to any disclaimer, the term of this patent is extended or adjusted under 35 U.S.C. 154(b) by 30 days.

(21) Appl. No.: 14/893,366

(22) PCT Filed: May 23, 2014

(86) PCT No.: PCT/EP2014/060737
§ 371 (c)(1),
(2) Date: Mar. 24, 2016

(87) PCT Pub. No.: WO2014/187993
PCT Pub. Date: Nov. 27, 2014

(65) Prior Publication Data
US 2016/0193284 A1    Jul. 7, 2016

(30) Foreign Application Priority Data

May 24, 2013  (FR) ...................................... 13 54691

(51) Int. Cl.
*A61K 35/741* (2015.01)
*A61K 38/12* (2006.01)
(Continued)

(52) U.S. Cl.
CPC .............. *A61K 38/12* (2013.01); *A23K 10/18* (2016.05); *A23K 20/195* (2016.05); *A23K 50/80* (2016.05);
(Continued)

(58) Field of Classification Search
CPC ................................................... A61K 35/741
See application file for complete search history.

(56) References Cited

FOREIGN PATENT DOCUMENTS

JP    2005298434 A  * 10/2005

OTHER PUBLICATIONS

English abstract of JP 2005-298434A.*
(Continued)

*Primary Examiner* — Rosanne Kosson
(74) *Attorney, Agent, or Firm* — Troutman Sanders LLP

(57) ABSTRACT

The present invention relates to an isolated bacterium from the genus *Pseudoalteromonas* for its use as a probiotic, the use of said strain as a preservative, cyclolipopeptides which may be obtained from this bacterium, a composition comprising at least such a cyclolipopeptide, as well as to their uses.

4 Claims, 2 Drawing Sheets

(51) Int. Cl.

| | |
|---|---|
| C07K 7/56 | (2006.01) |
| C11D 3/28 | (2006.01) |
| C11D 3/32 | (2006.01) |
| C11D 3/38 | (2006.01) |
| C11D 3/48 | (2006.01) |
| C12R 1/01 | (2006.01) |
| A23K 10/18 | (2016.01) |
| A23K 20/195 | (2016.01) |
| A23K 50/80 | (2016.01) |
| A61K 35/74 | (2015.01) |
| C07K 7/64 | (2006.01) |
| A61K 38/00 | (2006.01) |
| A61K 35/00 | (2006.01) |

(52) U.S. Cl.
CPC ............ *A61K 35/74* (2013.01); *A61K 35/741* (2013.01); *C07K 7/56* (2013.01); *C07K 7/64* (2013.01); *C11D 3/28* (2013.01); *C11D 3/32* (2013.01); *C11D 3/381* (2013.01); *C11D 3/48* (2013.01); *C12R 1/01* (2013.01); *A61K 38/00* (2013.01); *A61K 2035/11* (2013.01)

(56) References Cited

OTHER PUBLICATIONS

English translation of Sankyo Co. Ltd., JP 2005-298434A.*
Defer, et al: "Antimicrobial peptides in oyster hemolymph: The bacterial connection", Fish & Shellfish Immunology, vol. 34, No. 6, Mar. 22, 2013 (Mar. 22, 2013), pp. 1439-1447;—& Database EMBL [Online], Nov. 21, 2012 (Nov. 21, 2012), "Pseudoalteromonas sp. hCg-6 16S ribosomal RNA gene, partial sequence.", retrieved from EBI accession No. EM STD:JX912482, Database accession No. JX912482 sequence.
Balakirev, et al: "Symbiotic Associations in the Phenotypically-Diverse Brown Alga Saccharina japonica", PLOS One, vol. 7, No. 6, Jun. 20, 2012 (Jun. 20, 2012), p. e39587;—& Database EMBL [Online] Feb. 2012 (Feb. 2012), "Uncultured proteobacterium clone ncSPL071 16S ribosomal RNA gene, partial sequence.", retrieved from EBI accession No. EM STD:JQ218661, Database accession No. JQ218661 sequence.
Heindl, et al: "Phylogenetic diversity and antimicrobial activities of bryozoan-associated bacteria isolated from Mediterranean and Baltic Sea habitats", Systematic and Applied Microbiology, Urban & Fischer, Amsterdam, NL, vol. 33, No. 2, Mar. 2010 (Mar. 2010), pp. 94-104, [retrieved on Feb. 13, 2010]; —& Database EMBL [Online], Mar. 26, 2010 (Mar. 26, 2010), "Pseudoalteromonas sp. B201 partial 16S rRNA gene, strain B201", retrieved from EBI accession No. EM STD: FN295770 Database accession No. FN295770 sequence.
Kalinovskaya, et al: "a Pseudoalteromonas januariaa SUT 11 as the Source of Rare Lipodepsipeptides", Current Microbiology, Springer-Verlag, NE, vol. 56, No. 3, Jan. 8, 2008 (Jan. 8, 2008), pp. 199-207.
Bowman: "Bioactive Compound Synthetic Capacity and Ecological Significance of Marine Bacterial Genus *Pseudoalteromonas*", Marine Drugs, vol. 5, No. 4, Dec. 18, 2007 (Dec. 18, 2007), pp. 220-241.
Desriac, et al: "Bacteriocin as Weapons in the Marine Animal-Associated Bacteria Warfare: Inventory and Potential Applications as an Aquaculture Probiotic", Marine Drugs, vol. 8, No. 4, Jan. 2010 (Jan. 2010), pp. 1153-1177.
International Search Report dated Jul. 30, 2014 issued in corresponding PCT Application No. PCT/EP2014/060737.
French Search Report dated Jan. 15, 2014 issued in corresponding French Patent Application No. 1354691.
Wietz, et al: "Wide Distribution of Closely Related, Antibiotic-Producing Arthrobacter Strains throughout the Arctic Ocean", Applied and Environmental Microbiology, vol. 78, No. 6, Mar. 15, 2012 (Mar. 15, 2012), pp. 2039-2042; —& Database EMBL [Online], May 2, 2011 (May 2, 2011), "Pseudoalteromonas sp. MB33 16S ribosomal RNA gene, partial sequence.", retrieved from EBI accession No. EM STD:JF706643 Database accession No. JF706643 sequence; —& Database EMBL [Online] May 2, 2011 (May 2, 2011), "Pseudoalteromonas sp. MB205 16S ribosomal RNA gene, partial sequence.", retrieved from EBI accession No. EM STD:JF706645 Database accession No. JF706645 sequence; —& Database EMBL [Online] May 2, 2011 (May 2, 2011), "Pseudoalteromonas sp. MB220 16S ribosomal RNA gene, partial sequence.", retrieved from EBI accession No. EM STD: J F706646 Database accession No. JF706646 sequence, —Database EMBL [Online] May 2, 2011 (May 2, 2011), "Pseudoalteromonas sp. MB240 16S ribosomal RNA gene, partial sequence.", retrieved from EBI accession No. EM STD: J F706647 Database accession No. JF706647 sequence.

* cited by examiner

USE OF A BACTERIUM ISOLATED FROM THE GENUS *PSEUDOALTEROMONAS*, CYCLOLIPOPEPTIDES AND USES THEREOF

CROSS-REFERENCE TO RELATED APPLICATIONS

This application is the U.S. National Phase of International Patent Application Serial No. PCT/EP2014/060737, filed on May 23, 2014, which claims priority to French Patent Application No. FR1354691, filed on May 24, 2013, both of which applications are herein incorporated by reference in their entirety.

FIELD OF THE INVENTION

The present invention relates to an isolated bacterium from the genus *Pseudoalteromonas* for its use as a probiotic, to the use of said strain as a preservative, to cyclolipopeptides which may be obtained from this bacterium, to a composition comprising at least such a cyclolipopeptide, as well as to their uses.

BACKGROUND OF THE INVENTION

Aquaculture gathers all the animal or plant production activities in an aquatic medium. Aquaculture is practiced by the sea, in rivers or ponds. Certain systems of artificial reefs or attractor or concentration devices which may be assimilated to aquaculture, from the moment that there exists a direct offer of food or support (indirectly produced from a rise of water loaded with minerals for example). It also relates to the productions of fish (fish farming), of shell fish (shell fish farming), of crustaceans (astaciculture and shrimp farming), abalones (aquiculture), oysters (oyster farming) or further algae (algaculture).

Aquaculture is one of the responses brought to overfishing and to the increasing needs of fish. In 2008, it provided the world with 76.4% of fresh water fish, 68.2% of diadromous fish, 64.1% of molluscs, 46.4% of crustaceans and 2.6% of seawater fish consumed by humans.

It is sometimes used for other motives than food consumption, for example in Europe via many <<fish farming stations>> built from 1850 to 1870, or in Japan in order to reintroduce into the environment the shrimps or abalones where these animals have been overexploited or have disappeared for other causes (pollution . . . ).

Nowadays, intensification of the production methods and the weather variations have made the development of aquaculture and of oyster farming particularly vulnerable.

The use of probiotics from healthy wild animals is included in a natural bio-protection strategy for aquaculture species. If probiotics are widely used in farming, their use in aquaculture still remains a novelty.

The development of a biological and efficient strategy for protecting these species therefore appears as an undeniable asset for producers and industrialists of animal feeding.

Moreover, renewal of antimicrobial agents is today a priority of public and veterinary health. Their excessive and unsuitable use has led to the selection of multiresistant strains which cause therapeutic dead ends (25,000 deaths/year in the EEC, WHO 2011).

No new family of anti-Gram-negative antibiotic has been marketed for 30 years. The search for novel compounds having antimicrobial properties is therefore primordial and urgent.

In parallel, there also exists today a substantial need in the field of phytosanitary treatments for identifying alternative products, which are not noxious to the environment, but which remain efficient bactericidal agents.

SUMMARY OF THE INVENTION

Within the scope of the present invention, the inventors have isolated a marine bacterium having useful properties in the field of animal health, in particular in aquaculture.

This marine bacterium notably produces antibacterial compounds which the inventors have characterized at the structural and functional level.

This bacterium belongs to the genus *Pseudoalteromonas*.

The genus *Pseudoalteromonas* was first proposed by Gauthier et al. in 1995 and to this day consists of 39 species (Gauthier, G., Gauthier, M. & Christen, R. (1995). Phylogenetic Analysis of the Genera *Alteromonas, Shewanella*, and *Moritella* Using Genes Coding for Small-Subunit rRNA Sequences and Division of the Genus *Alteromonas* into Two Genera, *Alteromonas* (Emended) and *Pseudoalteromonas* gen. nov., and Proposal of Twelve New Species Combinations. Int J Syst Bacteriol 45, 755-761).

Thus, the inventors of the present application have isolated a *Pseudoalteromonas* hCg-6 bacterium, capable of producing antibacterial compounds, in particular cyclolipopeptides comprising a heptapeptide ring and a hydrocarbon chain of 4 to 20 carbon atoms, still more particularly cyclolipopeptides of formula A:

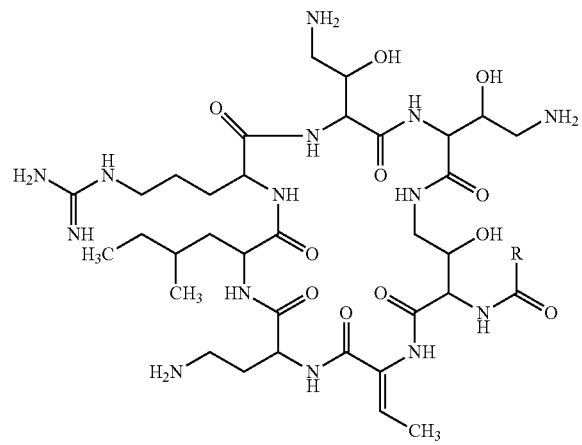

(A)

wherein:
R is selected from the group consisting of:
  alkyl groups comprising between 4 and 20 carbon atoms, except nonyl and undecyl groups; or
  alkylene groups comprising between 4 and 20 carbon atoms, except undec-4-ylene and tridec-6-ylene groups; or
  alkyl groups substituted with an —OH group and comprising between 4 and 20 carbon atoms; and
  alkylene groups substituted with an —OH group and comprising between 4 and 20 carbon atoms.

Still more particularly the isolated bacterium is the bacterium *Pseudoalteromonas* hCg-6, a strain deposited according to the Treaty of Budapest, May 22, 2013, at the Collection Nationale de Culture de Microorganismes (National collection of cultivated microorganisms) (CNCM, Paris, France), located at Institut Pasteur, 25, 28 rue du Docteur Roux, F-75724 Paris, France CEDEX 15, under number 1-4753. All restrictions imposed by the depositor on the availability to the public of the deposited material will be irrevocably removed upon the granting of the patent.

The strain hCg-6 was isolated from the hemolymph of the oyster *Crassostrea* and showed that it was capable of secreting antibacterial compounds in the hemolymph and the supernatant of various culture media.

By studying the genetic and biochemical features of this strain, it was possible to define a new species, as indicated in the following example.

Said bacterium is most particularly of interest insofar that it secretes in its culture supernatant, active antibacterial compounds against pathogenic bacteria, in particular in aquaculture or in the plant protection field.

According to one of these aspects, the present invention relates to the isolated bacterium as mentioned earlier for its use as a probiotic for animal breeding, in particular for aquaculture.

Still more particularly, the present invention relates to the isolated bacterium as mentioned above for its use as a probiotic for fish farming, shell fish farming, aquiculture, astaciculture, shrimp farming, oyster farming and algaculture. Still more particularly, the present invention relates to the isolated bacterium as mentioned above for its use for improving the health of fish, shellfish, crustaceans, abalones, oysters or further algae.

The present invention also relates to the use of the isolated bacterium as mentioned above as a probiotic, in particular for fish farming, shellfish farming, astaciculture, shrimp farming, aquiculture, oyster farming and algaculture. Still more particularly, the present invention relates to the use of the isolated bacterium as mentioned above for improving the health of fish, shellfish, crustaceans, abalones, oysters or further algae.

The present invention, according to another of these aspects, also relates to a method for treating fish, shellfish, crustaceans, abalones, oysters or further algae, which comprises the administration of an effective amount of a bacterium according to the invention. In particular, this method is intended to improve the health of fish, shellfish, crustaceans, abalones, oysters or further algae.

By <<probiotic>>, is meant a food additive comprising an effective amount of the isolated bacterium according to the invention, intended to be introduced into the food of animals. According to the OMS, probiotics are live microorganisms which administered in a suitable amount, give the host a benefit on its health (WHO, 2001).

By <<effective amount>>, is meant an amount of bacterium which allows demonstration of the sought effect. In particular, an amount comprised between $10^3$ and $10^{10}$ CFU·ml$^{-1}$ is meant.

According to another of these aspects, the present invention also relates to the use of a bacterium as mentioned earlier, as a phytosanitary agent.

The present invention, according to another of these aspects, also relates to a phytosanitary treatment method, which comprises the administration of an effective amount of a bacterium according to the invention, in particular to a plant, a fungus or an insect.

Moreover, the inventors have isolated an original family of cyclolipopeptides. The cyclolipopeptides according to the invention comprise a heptapeptide ring acylated by a hydrocarbon chain with variable length, unsaturation and hydroxylation level.

Thus, the present invention also relates to a cyclolipopeptide of formula A:

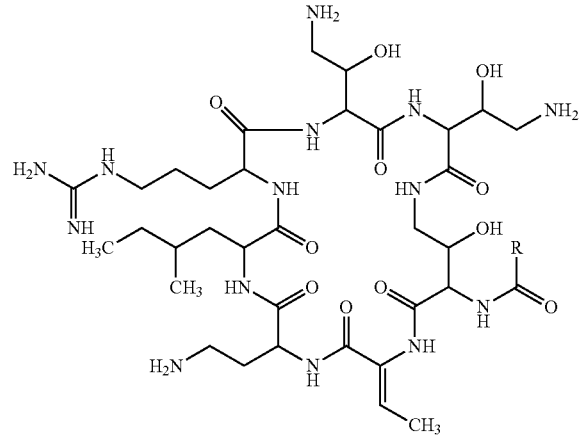

(A)

wherein:
R is selected from the group consisting of:
  alkyl groups comprising between 4 and 20 carbon atoms, except nonyl and undecyl groups; or
  alkylene groups comprising between 4 and 20 carbon atoms, except undec-4-ylene and tridec-6-ylene groups; or
  alkyl groups substituted with an —OH group and comprising between 4 and 20 carbon atoms; and
  alkylene groups substituted with an —OH group and comprising between 4 and 20 carbon atoms.

By <<alkyl>> group, is meant a linear or branched, optionally cyclic saturated aliphatic group, comprising between 4 and 20 carbon atoms, more particularly between 6 and 14 carbon atoms. As examples, mention may be made of butyl, pentyl, hexyl, heptyl, octyl, decyl, dodecyl and tridecyl groups, etc.

By <<alkylene>> group, is meant a linear or branched, optionally cyclic unsaturated aliphatic group, comprising between 4 and 20 carbon atoms, more particularly between 6 and 14 carbon atoms, and including one or several double bonds, notably 1 to 3. As examples, mention may be made of butylene, pentylene, hexylene, heptylene, octylene, nonylene, decylene, undecylene, dodecylene, tridecylene groups, etc. In particular, mention may be made of a nonylene, in particular a nonyl-2-ene, an octylene, a decylene, a dodecylene, a decyldiene, a tridecyltriene group, etc.

As an alkyl group substituted with an —OH group, mention may for example be made of a nonanol, in particular a nonan-2-ol.

As an alkylene group substituted with an —OH group, mention may for example be made of an octenol.

More particularly, the cyclolipopeptide according to the invention is a cyclolipopeptide of formula (A), as mentioned above, wherein R is selected from the group consisting of:
  alkyl groups comprising between 6 and 14 carbon atoms, except nonyl and undecyl groups; or
  alkylene groups comprising between 6 and 14 carbon atoms, except undec-4-ylene and tridec-6-ylene groups; or
  alkyl groups substituted with an —OH group and comprising between 6 and 14 carbon atoms; and alkylene groups substituted with an —OH group and comprising between 6 and 14 carbon atoms.

Still more particularly, the cyclolipopeptide according to the invention is selected from cyclolipopeptides of formula (A), as defined above, wherein R is selected from the group consisting of the groups: nonylene, in particular nonyl-2-ene, nonanol, in particular nonan-2-ol, heptyl, octylene, octyl, decanyl, decanol, decyldiene, decylene, octenol, dodecylene and tridecyltriene.

According to one of the aspects of the present invention, the cyclolipopeptide described in the present application may be obtained from a bacterium as described within the scope of the present invention.

Thus, the present invention also relates to a method for producing a cyclolipopeptide as defined above, comprising a step for cultivating a bacterium as described earlier, under conditions allowing the production of said cyclolipopeptides.

In particular, the bacterium is cultivated under conditions which will be adapted by one skilled in the art who will know how to determine the culture conditions, notably the culture temperature, ideal for the production of the cyclolipopeptides.

More particularly, the bacterium is cultivated for 24 to 96 hours, preferably for 72 hours, at a temperature comprised between 4 and 25° C., preferably between 12 and 18° C., with stirring at a rate comprised between 70 and 130 rpm, preferably 100 rpm.

The culture medium is in particular the marine broth medium (Difco®) or a synthetic medium called F29 medium containing a phosphate buffer 47 mM, pH 7.4 (7.6 g $K_2HPO_4$, 3 g of $KH_2PO_4$-Sigma®), 3% of marine salts (SeaSalts-Sigma®), 50 mM of saccharose and 20 ml of MEM 50× per liter, preferably the synthetic medium F29.

According to one of these aspects, the production method also comprises a step for isolating cyclolipopeptides, following the cultivation step of the bacterium. In particular, this isolation is achieved by harvesting the culture supernatant, for example by centrifugation of the latter.

According to one of these aspects, the production method also comprises a step for purifying cyclolipopeptides, following the isolation step mentioned earlier.

In particular, the purification is achieved with any suitable chromatographic method for one skilled in the art, such as for example by a combination of liquid chromatography coupled with bio-functional analysis.

Thus, according to one of these aspects, the method for producing cyclolipopeptides according to the invention comprises the following steps:

a) cultivating a bacterium as described within the scope of the present invention under conditions allowing the production of cyclolipopeptides, in particular in the culture medium F29 as described within the scope of the present invention; and/or b) isolation of the cyclolipopeptides; and/or c) purification of the cyclolipopeptides.

The cyclolipopeptides according to the invention have a powerful and selective activity for gram-negative bacteria.

Thus, the present invention also relates to at least one cyclolipopeptide according to the invention, for its use as a drug. More particularly, the invention relates to a cyclolipopeptide according to the invention, for its use as a drug.

According to one of these aspects, the invention also relates to at least one cyclolipopeptide according to the invention, for its use as an antimicrobial agent. More particularly, the invention relates to a cyclolipopeptide according to the invention, for its use as an antimicrobial agent.

In particular, said cyclolipopeptide(s) is(are) used for cleaning the skin, more particularly for cleaning hands, or as an active agent in hygiene products, more particularly body hygiene products.

The present invention, according to another of these aspects, also relates to a treatment method which comprises the administration of an effective amount of at least one cyclolipopeptide according to the invention, in particular of a cyclolipopeptide according to the invention. Said treatment method is in particular a method for antibacterial treatment, notably for cleaning the skin, for washing hands, or for body hygiene.

According to another of these aspects, the present invention also relates to the use of at least one cyclolipopeptide according to the invention, as a phytosanitary agent, in particular for protecting plants, fungi and insects. More particularly, the invention relates to the use of a cyclolipopeptide as a phytosanitary agent, in particular for protecting plants, fungi and insects. The present invention, according to another of these aspects, also relates to a phytosanitary treatment method, which comprises the administration of an effective amount of at least one cyclolipopeptide according to the invention, in particular of a cyclolipopeptide according to the invention, in particular to a plant, a fungus or an insect.

According to further another of these aspects, the present invention also relates to the use of at least one cyclolipopeptide according to the invention, as a preservative for the agro-food industry or the cosmetic industry.

According to another of these aspects, the present invention relates to a method for improving the preservation of product(s) intended for the agro-food industry or the cosmetic industry, which comprises the adjunction of at least one cyclolipopeptide according to the invention to the product(s) to be preserved.

According to still further another of these aspects, the present invention relates to a cosmetic and/or dermatological composition comprising at least one cyclolipopeptide according to the invention in a physiologically acceptable carrier. Preferably, said compositions comprise a cyclolipopeptide according to the invention. More particularly, said cyclolipopeptide(s) is(are) combined with an adjuvant or a solvent.

By <<cosmetic composition>> is meant a substance or a preparation intended to be put into contact with various surface portions of the human body, notably the epidermis, the hair and capillary systems, the nails, the lips and the external genital organs, or with the teeth and buccal mucosa, in order, either exclusively or mainly, to clean them, to beautify them, to perfume them, to modify the aspect thereof, to protect them, to maintain them in good condition or to correct body odors.

By <<dermatological composition>> is meant a substance or preparation intended to be put into contact with various surface portions of the human body, notably the epidermis, the hair and capillary systems, the nails, the lips and the external genital organs, or with the teeth and buccal mucosa, in order to prevent and/or treat skin pathologies. A dermatological composition is intended for therapeutic use.

The present invention also relates to a pharmaceutical composition comprising at least one cyclolipopeptide according to the invention in a pharmaceutically acceptable carrier. Preferably, said composition comprises a cyclolipopeptide according to the invention. More particularly, said cyclolipopeptide(s) is(are) combined with an adjuvant or solvent.

Thus, a cyclolipopeptide according to the present invention may be used both in applications intended for food, more specifically in the field of preserving food stuffs, and in applications intended for the human being, such as a drug, or as a dermatological agent giving the possibility of removing microbial agents, bacteria, notably those present at the surface of the skin, and more particularly on hands. A cyclolipopeptide according to the present invention may also be used in the cosmetic field. It may moreover be used in phytosanitary applications.

The pharmaceutically acceptable excipients are selected according to the pharmaceutical form and the desired administration method, from among the customary excipients which are known to one skilled in the art.

In the pharmaceutical compositions of the present invention for oral, sublingual, subcutaneous, intramuscular, intravenous, topical, local, intratracheal, intranasal, transdermal or rectal administration, the cyclolipopeptides as defined above, may be administered as unit dosage forms, mixed with standard pharmaceutical excipients, to animals and to human beings.

The suitable administration forms comprise the oral route forms such as tablets, soft or hard gelatine capsules, powders, granules and oral solutions or suspensions, the sublingual, buccal, intratracheal, intraocular, intranasal, by inhalation administration forms, the topical, parenteral administration forms such as transdermal, subcutaneous, intramuscular or intravenous forms, rectal administration forms and implants. For topical application, it is possible to use the cyclolipopeptides according to the invention in creams, gels, ointments or lotions.

When a solid composition in the form of tablets is prepared, the cyclolipopeptide may be mixed with a pharmaceutical carrier, such as gelatin, starch, lactose, magnesium stearate, talcum, gum arabic or the like.

The tablets may also be coated with saccharose, a cellulose derivative, or other suitable materials or further they may be treated so that they have a prolonged or delayed activity and that they continuously release a predetermined amount of active ingredient.

A preparation as gelatin capsules may for example be obtained by mixing the active ingredient with a dilutant and by pouring the obtained mixture into soft or hard gelatin capsules.

The pharmaceutical compositions containing a cyclolipopeptide according to the invention, may also appear in liquid form, for example as solutions, emulsions, suspensions or syrups, and notably in a suitable form for oral or intranasal administration, for example. The suitable liquid supports may for example be water, organic solvents such as glycerol or glycols, as well as mixtures thereof, in varied proportions, in water.

A preparation as a syrup or elixir or for administration as drops may also contain the active ingredient together with a sweetener, for example an acaloric sweetener, as well as an agent providing taste and a suitable coloring agent.

The powders or granules dispersible in water may for example contain the active ingredient in a mixture with dispersion agents or wetting agents, or suspending agents, like polyvinylpyrrolidone, as well as with sweeteners or taste correctors.

The amount administered per day to each patient, human or animal will be determined, according to usual practice, by the physician or the veterinarian according to the administration method, the weight and the response of said patient. Generally, the daily amount of the cyclolipopeptide according to the invention will be the smallest effective amount of cyclolipopeptide capable of producing the sought therapeutic effect.

By <<effective amount>>, is meant any amount of a composition which improves one or several of the effectiveness parameters sought.

There may be particular cases when higher or lower dosages are suitable; such dosages do not depart from the scope of the present invention.

In the cosmetic or dermatological compositions according to the invention, the physiologically acceptable excipients are selected according to the cosmetic or dermatological form and the desired administration method, from among the customary excipients which are known to one skilled in the art.

A physiologically acceptable medium is a non-toxic medium and may be applied on the skin and the appendages of human beings and with a pleasant aspect, odor and touch.

For administration via an oral route, the cosmetic or dermatological composition according to the invention may appear in any suitable form, in particular in the form of a drinkable solution, of a tablet, of a gelatin capsule, of a capsule or further of a foodstuff or nutritional supplement.

For topical application on the skin, the composition may notably have the form of aqueous or oily solutions or dispersions of the lotion or serum type, of emulsions with liquid or semi-liquid consistency of the milk type, obtained by dispersing a fatty phase in an aqueous phase (O/W) or vice versa (W/O), or suspensions or emulsions with soft consistency of the aqueous or anhydrous gel or cream type, or further of microcapsules or microparticles, or of vesicle dispersions of the ionic and/or non-ionic type or of foams. These compositions are prepared according to customary methods.

The amounts of cyclolipopeptides in the cosmetic or dermatological compositions according to the invention will be comprised between 0.1% and 3%, preferably between 0.2% and 0.5%.

The cosmetic or dermatological compositions according to the invention may for example form cleaning, protective, treating or care creams for the face, for hands, for feet, for large anatomic folds or for the body (for example day care creams, night care creams), body care or protective milks, lotions, gels or foams for the care of the skin, like cleaning lotions, deodorizing compositions.

The compositions may also consist in solid preparations forming soaps or cleaning bars.

The compositions may also be packaged as a composition for an aerosol also comprising a pressurized propellant.

In particular, the dermatological or cosmetic composition according to the invention may be selected from deodorants or cleaning milks or foaming gels. The following figures and examples illustrate the present invention without limiting the scope thereof.

Figure 1:
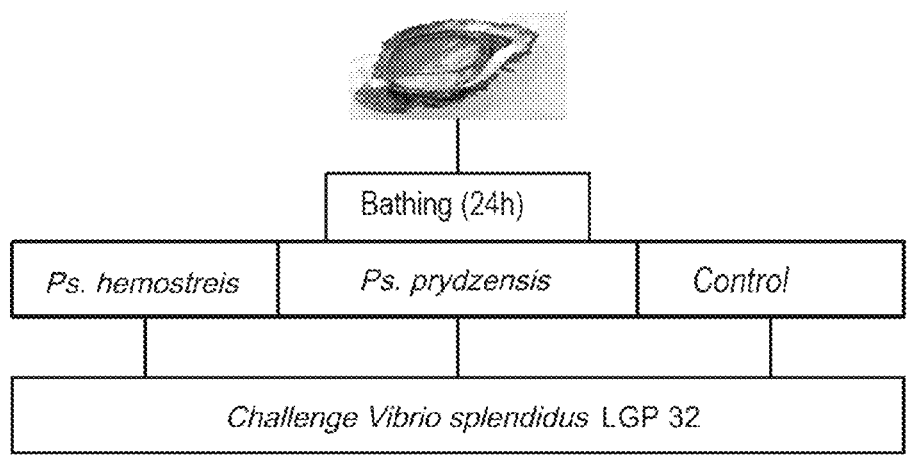
FIG. 1: Experimental procedure set into place in order to evaluate the effects of the strain hCg-6 on the survival of oyster spat.

(A): Control dish, untreated and not sown,
(B) and (C): dishes not treated with the sample and respectively sown with *E. coli* ATCC 25922 and *E. coli* P7,
(D) and (E): dishes treated with 200 μg of cyclolipopeptides according to the invention and respectively sown with *E. coli* ATCC 25922 and *E. coli* P7.

DETAILED DESCRIPTION OF THE INVENTION

Examples (i) Isolation and Identification of the Strain *Pseudoalteromonas* hCg-6

The bacterial strain hCg-6 was isolated from the hemolymph of *Crassostrea gigas*.

These oysters are harvested in the Rhuys peninsula in the Golf of Morbihan, France (47° 30'50 North, 2° 37'50 West, WGS84 system). After carefully opening the oysters, the hemolymph is collected in the pericardial cavity by using a sterile needle for single use. For bacterial isolation, each individual sample of hemolymph (1.5 ml) is directly laid on marine agar (Difco® 2216) by means of an automatic sowing machine (WASP, AES Chemunex, France) and incubated for 72 h at 18° C.

By studying the genetic and biochemical features of hCg-6, it is possible to define a new species.

The studies of mobility and relating to the morphology were conducted by using an optical microscope (Olympus BX50). The capability of the bacterial strain of hydrolyzing Tween 40 and 80 was tested according to the Lelliot and Stead method (1987). The enzymatic activities and the biochemical features were determined by using the following kits: API 20 E, API 50 CH and API ZYM (Biomérieux) according to the conditions indicated by the supplier. According to the indications of Park et al. (2005), the media provided by Biomérieux used in the inoculation kits were completed with 2% w/v of sea salts (Sigma). Finally, the analyses relating to the fatty acid constitution were conducted according to the method described in Kämpfer & Kroppenstedt, 1996; Kuykendall et al., 1988; Miller, 1982.

Thus it was possible to determine that this Gram-negative bacterium did not form spores, is a mobile organism (0.6-0.9 μm in width, 1.9-3 μm in length), capable of forming colonies slightly colored in brown.

Growth is observed between 4 and 30° C. (optimum growth between 25 and 30° C.).

The main fatty acids which make it up are the following: 3=C16:1 ω7c/i-C15:0 2-OH (36.6%), C18:1ω7c (18.6%), C16:0 (13.8%).

The other physiological and biochemical characteristics of the bacterial strain hCg-6 are gathered in Table 1 below. In addition to these results, it was also determined that the strain is a catalase−, oxidase+, and hydrolyzes Tween 40 and 80. During the analyses using the kit API ZYM, the strain hCg-6 showed positive reaction to alkaline phosphatase, acid phosphatase, naphthol-AS-BI-phosphohydrolase, alpha-glucosidase and N-acetyl-beta-glucosaminidase. An absence of reaction was observed for the other enzymatic activities included in the kit API ZYM. Following the analyses conducted with the kit API 20 NE, the following tests are positive: reduction of the nitrate, hydrolysis of esculin, assimilation of glucose, maltose, N-acetyl-glucosamine, malate and citrate. The following substances are not used: D-galactose, L-rhamnose, D-sorbitol, D or L-arabinose, D or L-arabitol and D-melibiose. The bacterial strain hCg-6 uses glucose, saccharose, trehalose, fructose, D-cellobiose and D-maltose as sources of carbon and of energy.

The strain is resistant to polymyxin (50 μg) and to cephalexin but sensitive to enrofloxacin, cefquinom 30, gentamycin, oxolinic acid, tetracycline and amoxicillin.

TABLE 1

Physiological and biochemical features of the strain hCg-6:

| Characteristics | hCg-6 |
|---|---|
| DNA G + C composition (mol %) | 41.2 |
| Pigmentation | f |
| Growth at/in: | |
| 4° C. | + |
| 37° C. | − |
| 0.5% NaCl | + |
| ≥12% NaCl | − |
| Hydrolysis of starch | − |
| Use of: | |
| D-glucose | + |
| D-fructose | + |
| D-arabinose | − |
| Glycerol | − |
| Mannose | + |
| D-mannitol | − |
| Citrate | + |
| N-acetyl-glucosamine | + |
| Sensitive to: | |
| Polymyxin (300 ED) | − |

+, Positive;
−, negative;
f: slight reaction

This strain was subject to deposition registered according to the Budapest Treaty, on May 22, 2013, at the Collection Nationale de Culture de Microorganismes (CNCM, Paris, France) under the number I-4753.

(ii) Activity of the *Pseudoalteromonas* hCg-6 Strain in Aquaculture

In order to evaluate the role of bioprotection of the strain hCg-6, experimental infections with *Vibrio splendidus* LGP32 (injection into the adductor muscle) of naive diploid oysters (18 months old spat) were carried out with or without preliminary bathing with the strain hCg-6. The experimental procedure is shown in FIG. 1.

Figure 2:
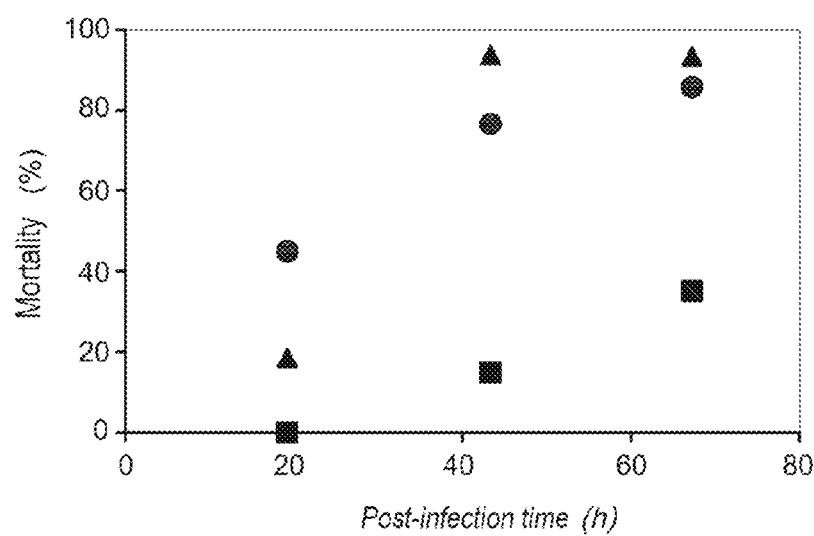
FIG. 2: Change in the mortality of naïve diploid oysters in the presence of a pathogen (*Vibrio splendidus* LGP32) without (●) or with preliminary bathing with the strain *Pseudoalteromonas* hCg-6 (■) and *Pseudoalteromonas prydzensis* (▲).

The results show that preliminary bathing of the oysters (n=19) in the presence of the hCg-6 strain results in a significant reduction in the mortality (FIG. 2). Indeed, after 60 h, the overall mortality is stabilized to 35% while the batch of unbathed oysters (n=22) with hCg-6 has a mortality level of 86% and 94% for those (n=16) bathed with the *Pseudoalteromonas prydzensis* strain (control).

(iii) Production and Isolation of Cyclolipopeptides

After cultivating the strain *Pseudoalteromonas* hCg-6 for 72 h at 18° C. with stirring (100 rpm) in the synthetic medium F29 (phosphate buffer 47 mM, pH 7.4 (7.6 g $K_2HPO_4$, 3 g $KH_2PO_4$-Sigma®), 3% of marine salts (Sea-Salts-Sigma®), 50 mM of saccharose and 20 ml of MEM 50× per liter), the culture supernatant, containing the active molecules is harvested by centrifugation for 30 minutes at 7,500 rpm at 4° C. A combination of liquid chromatographies coupled with bio-functional analyses is implemented in order to purify the active compounds present in the culture supernatant. Two solvents are used: $H_2O$ milliQ 0.07% TFA (Sigma®) (solvent A) and acetonitrile (Carlo Erba®) 0.07% TFA (solvent B). The culture supernatant is deposited on an SPE column (Upti Clean columns C18-S-Interchim®) packaged beforehand according to the instructions of the supplier. After washing the column with a mixture of the solvents A and B (90/10), elution is ensured by a mixture of solvents A and B 60-40 (v/v).

The eluted fraction is then analyzed in reverse phase chromatography on an HTec column (250 mm×4.6 mm-Macherey-Nagel®). The elution is tracked at 220 and 280 nm and ensured by a biphasic linear gradient of solvent B (20 to 28% within 8 mins and then 28 to 33% within 15 mins) at a flow rate of 0.8 ml·min-1 at 40° C. The absorbance peaks are manually collected, freeze-dried, tested for their antibacterial activity and stored at −20° C. A series of 11 bioactive compounds having different retention times was thus purified and analyzed by mass spectrometry (MALDI TOF/TOF Autoflex III smartbeam (Bruker Daltonics), matrix used: HCCA, low mass or LIFT method).

The molecular masses of the molecular ions (M+H+) of the active compounds are the following: 927, 971, 941, 953, 939, 967, 965, 985, 995, 1005 and 968.

(iv) Structural Characterization of the Cyclolipopeptides

Structural characterization of the 11 bioactive compounds was conducted by nuclear magnetic resonance (NMR) and mass spectrometry (Maldi-TOF/TOF).

The samples analysed by NMR contain about 1 mM of peptide dissolved in water (90% $H_2O$ and 10% $D_2O$), at pH 5. The NMR spectra were recorded at 298K on an NMR Bruker Avance 500 spectrometer, equipped with a cryoprobe TXI 5 mm triple resonance ($^1H$, $^{13}C$, $^{15}N$).

The assignment of the chemical shifts was carried out by means of standard sequences (Bruker) of homonuclear and heteronuclear 1D and 2D spectra: TOCSY, NOESY, $^{13}C$-HSQC and $^{13}C$-HMBC. A relaxation time of 1.4 s was used for all the experiments and mixing times of 100 ms and 250 ms for the TOCSY and NOESY experiments, respectively. Sizes of matrices of 2K or 4K in F2 and 320K to 400K in the F1 dimension were used. 8 to 32 scans were accumulated for each value of t1.

The chemical shifts are calibrated through the residual chemical shift of water. The TOPSPIN software was used for treating the obtained spectra.

The analyses showed that the 11 compounds are of a lipopeptide nature. They consist of a heptapeptide cycle acylated by a hydrocarbon chain varying in length (8 to 14 carbon atoms), unsaturation level and in hydroxylation, as indicated in table 2 below.

(v) Action Mechanism of the Cyclolipopeptides

The cyclolipopeptide no. 2 was tested on a collection of strains of *Vibrio splendidus* isolated from oysters. It has minimum inhibitory concentrations from 1.56 to 50 µM. The MICs were defined in a liquid medium by using the procedure of Wiegand, Hilpert, and Hancock 2008.

In a first phase, a loss in cultivability of the oyster pathogen *V. splendidus* LGP32 was observed in the presence of the cyclolipopeptide, suggesting a bactericidal effect. By flow cytometry analysis (FacsCalibur), the bactericidal activity on the bacteria was confirmed by using double-labeling with Syto9 and with propidium iodide (an indicator of permeabilization of bacterial membranes).

The detail of the action mechanism was revealed by flow cytometry by means of other fluorescent markers of a physiological state. Thus, the loss of cultivability of the strain LGP32 exposed to the cyclolipopeptide, is correlated with stopping of the membrane breathing (revealed by marking with CTC) and depolarization of the cytoplasmic membrane (which becomes permeable to diBAC). Moreover, the total number of cells of LGP32 (revealed by marking with SyberGreen I) decreases with exposure to the cyclolipopeptide, referring to a lytic effect.

The capability of the cyclolipopeptides according to the invention of binding the bacterial lipopolysaccharide (LPS) was measured by means of the color-forming test "limulus amebocyte lysate assay". The cyclolipopeptides according to the invention have demonstrated strong affinity for the LPS of *E. coli*. The affinity of the cyclolipopeptides according to the invention for the LPS of *E. coli* was quantified by thermophoresis at a microscale, the apparent dissociation constant was estimated to be 10.4 µM+/−680 nM.

TABLE 2

Structure of the cyclolipopeptides produced by the strain *Pseudoalteromonas* hCg-6

| General structure of the cyclolipopeptides | No R |
|---|---|
| [chemical structure] | 1 C10:1* |
| | 2 C10:0-OH ** |
| | 3 C8:0 |
| | 4 C9:1 |
| | 5 C9:0 |
| | 6 C11:2 |
| | 7 C11:1 |
| | 8 C11:0-OH** |
| | 9 C13:1 |
| | 10 C14:3 |
| | 11 C11:0 |

*the double bond is in position 3, cis configuration
**the OH group is in position 3

(vi) Biological Activity of the Cyclolipopeptides

The minimum inhibitory concentration (MIC) of the compounds nos. 1, 2, 3, 5, 7 and 8 was evaluated in a liquid medium following the procedure of Wiegand, Hilpert, and Hancock 2008. The spectrum of the target bacteria was extended to certain human pathogens such as the bacteria *Salmonella enterica*, a clinical strain of *Escherichia coli* having a beta-3-lactamase activity with an extended spectrum and *Pseudomonas aeruginosa*. After 24 h of incubation at an optimum temperature, the MICs are evaluated visually.

The results show that the cyclolipopeptides have an activity specifically directed against the negative Gram bacteria (Table 3). The obtained MICs are of the order of the µM.

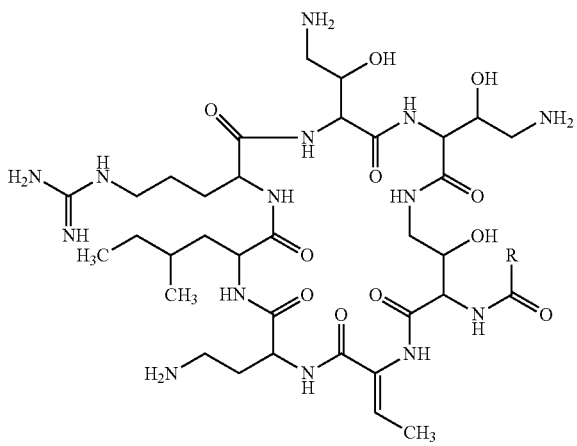

(A)

TABLE 3

| Activity spectrum of the cyclolipopeptides nos. 1, 2, 3, 5, 7 and 8 (MIC) | | 3 | 5 | 1 | 2 | 7 | 8 | *Polymyxin B* |
|---|---|---|---|---|---|---|---|---|
| *Lactococcus garviae* | ATCC 43921 | ND | ND | — | — | ND | ND | ND |
| *Listeria monocytogenes* | SOR200 | ND | ND | — | — | ND | ND | ND |
| *Staphylococcus aureus* | ATCC 25923 | ND | ND | — | — | ND | ND | ND |
| *A. caviae* | CIP 7616 | ND | ND | ND | 17.6 | ND | ND | 3.1 |
| *A. hydrophila* | CIP 7614 | — | 25 | ND | ND | — | — | 0.8 |
| *E. coli* β résistante | P7 (clinical strain) | ND | ND | 3.1 | 8.8 | ND | ND | 1.6 |
| *E. coli* | ML35 | 100 | 50 | 12.5 | 35 | — | — | 3.1 |
| *E. coli* | SBS363 | 50 | 25 | 0.2 | 0.1 | 100 | — | 0.2 |
| *Pseudomonas aeruginosa* | ATCC 27853 | — | — | — | 35.2 | 100 | — | 1.6 |
| *S. enterica* | CIP 8297 | 12.5 | 6.3 | 0.7 | 1.4 | 25 | 100 | 0.8 |
| *V. harveyi* | ORM4 | 50 | 6.3 | 12.5 | ND | 50 | 50 | 25 |
| *V. splendidus* | LGP 32 | 50 | 6.3 | 12.5 | 4.4 | 50 | 50 | 1.6 |
| *Y. ruckeri* | ATCC 29473 | 50 | 6.3 | 0.4 | 1.1 | 0.4 | 50 | 0.4 |

The results obtained with the strains of *E. coli* ML35 and SBS363 suggest a role of the components of the external membrane in the sensitivity to cyclolipopeptides. Indeed, the strain SBS363 exposes an LPS with a short chain compared to that of the strain ML35. In every case, this structural modification results in an increase in the antibacterial activity of the cyclolipopeptides.

The defined MICs are comparable with those of polymyxin B also called colistin.

The cytotoxic activity of the cyclolipopeptides according to the invention was also evaluated by the test with MTT (tetrazolium salt MTT) on the cell line of a fibroblast 3T3. The results show a dose-dependent increase in the cytotoxicity. Nevertheless, it remains less than 50% for concentrations close to 200 µM.

(vii) Activity of the Cyclolipopeptides in Dermatology

Figure 3:
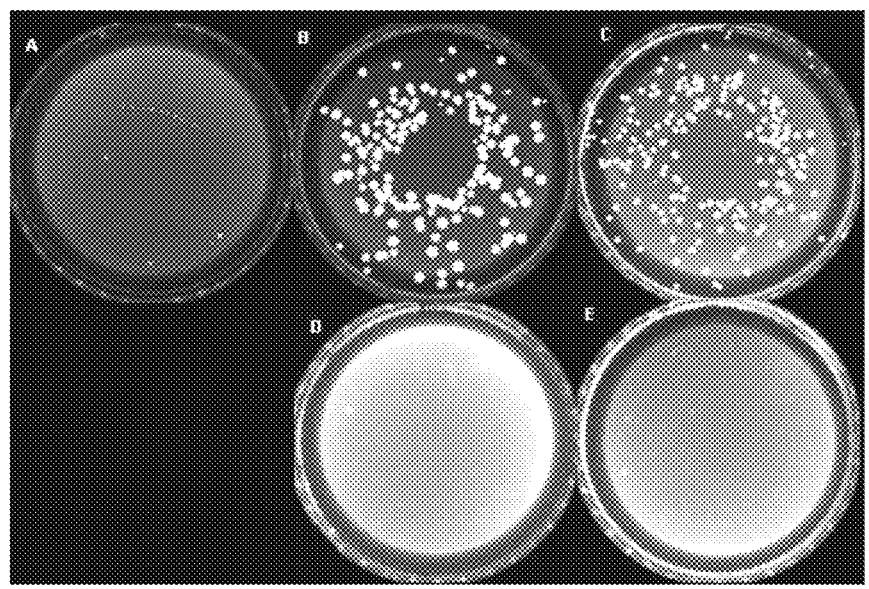
FIG. 3: Evaluation of the antibacterial cleaning power of cyclolipopeptides according to the invention with the RAPA test.

The antibacterial power of the cyclolipopeptides according to the invention was evaluated by the RAPA test (Ansari et al, Int. J.Cosmetic Sci, 2010, 33:107-10). In order to simulate washing of hands, Petri dishes containing Trytone Soy Agar (TSA) are used. The TSA is manually washed with the sample (45 seconds) and then rinsed with water and dried in air. The target bacteria (200 CFU) are subsequently deposited. The dishes are incubated at an optimum growth temperature. The results show that the cyclolipopeptides according to the invention have a real antibacterial cleaning power (FIG. 3).

The invention claimed is:

1. A method of treatment to improve animal breeding, which comprises the administration of an effective amount of an isolated bacterium *Pseudoalteromonas* hCg-6, capable of producing cyclolipopeptides or formula A:

wherein:
R is selected from the group consisting of
(a) alkyl groups comprising between 4 and 20 carbon atoms, except nonyl and undecyl groups;
(b) alkylene groups comprising between 4 and 20 carbon atoms, except undec-4-ylene and tridec-6-ylene groups;
(c) alkyl groups substituted with an —OH group and comprising between 4 and 20 carbon atoms; and
(d) alkylene groups substituted with an —OH group and comprising between 4 and 20 carbon atoms.

2. The method according to claim 1, wherein the isolated bacterium is *Pseudoalteromonas* hCg-6, a strain deposited according to the Budapest Treaty, on May 22, 2013, at the Collection Nationale de Culture de Microorganismes (CNCM, Paris, France) under the number I-4753.

3. The method of claim 1, wherein the animal breeding occurs in aquaculture.

4. The method of claim 1, wherein the animal is a fish, shellfish, crustacean, abalone or oyster.

* * * * *